United States Patent
Kouji et al.

(10) Patent No.: US 9,702,828 B2
(45) Date of Patent: Jul. 11, 2017

(54) PINHOLE INSPECTION APPARATUS FOR CAN BODIES

(71) Applicant: TOYO SEIKAN GROUP HOLDINGS, LTD., Tokyo (JP)

(72) Inventors: Yasuhiro Kouji, Yokohama (JP); Tomoki Seo, Sendai (JP); Yuuma Ishii, Ibaraki (JP)

(73) Assignee: TOYO SEIKAN GROUP HOLDINGS, LTD., Tokyo (JP)

( * ) Notice: Subject to any disclaimer, the term of this patent is extended or adjusted under 35 U.S.C. 154(b) by 320 days.

(21) Appl. No.: 14/428,030

(22) PCT Filed: Sep. 5, 2013

(86) PCT No.: PCT/JP2013/073981
§ 371 (c)(1),
(2) Date: Mar. 13, 2015

(87) PCT Pub. No.: WO2014/045890
PCT Pub. Date: Mar. 27, 2014

(65) Prior Publication Data
US 2015/0253260 A1    Sep. 10, 2015

(30) Foreign Application Priority Data
Sep. 18, 2012  (JP) .................. 2012-204574

(51) Int. Cl.
*G01M 3/38* (2006.01)
*G01N 21/894* (2006.01)
*G01N 21/90* (2006.01)

(52) U.S. Cl.
CPC .............. *G01N 21/90* (2013.01); *G01M 3/38* (2013.01); *G01N 21/894* (2013.01); *G01N 21/909* (2013.01)

(58) Field of Classification Search
None
See application file for complete search history.

(56) References Cited

U.S. PATENT DOCUMENTS 4,455,225 A    6/1984   Morimoto et al.

FOREIGN PATENT DOCUMENTS

| EP | 2 866 023 A1 | 4/2015 |
|---|---|---|
| JP | 57-7545 A | 1/1982 |

(Continued)

OTHER PUBLICATIONS

International Search Report dated Dec. 10, 2013, issued in corresponding application No. PCT/JP2013/073981.

*Primary Examiner* — Kara E Geisel
*Assistant Examiner* — Amanda Merlino
(74) *Attorney, Agent, or Firm* — Westerman, Hattori, Daniels & Adrian, LLP

(57) ABSTRACT

The present invention provides a pinhole inspection apparatus for can bodies including a rotary plate having a penetrating through hole, a movable plate provided on a stationary frame opposite the rotary plate, a can body holding member that holds a can body, a photodetector that detects light leaking inside the can body, and a light source that irradiates an outer circumferential surface of the can body with light. The movable plate includes a ring plate attached to a front surface of a piston member, which has a penetrating hole in a central portion thereof, via a joint member. The ring plate is provided with a shield member formed by an annular member that is formed concentric to the penetrating hole. The shield member is brought into sliding contact with the rotary plate by a pressure application mechanism.

7 Claims, 7 Drawing Sheets

(56) References Cited

FOREIGN PATENT DOCUMENTS

| JP | 6-109661 A | 4/1994 |
|---|---|---|
| JP | 2002-365230 A | 12/2002 |
| JP | 2003-75360 A | 3/2003 |
| JP | 2004-317356 A | 11/2004 |
| JP | 2009-25131 A | 2/2009 |
| JP | 4230269 B2 | 2/2009 |
| JP | 4715988 B2 | 7/2011 |

Prior Art

PINHOLE INSPECTION APPARATUS FOR CAN BODIES

TECHNICAL FIELD

The present invention relates to an apparatus for inspecting pinholes formed in a body part or the like of the can bodies.

BACKGROUND ART

During a production process of metal can bodies such as seamless can bodies produced by drawing with ironing (hereinafter simply referred to as "can body"), pinholes in the form of holes or cracks may be created in a body part or the like of the can body. Commonly, presence or absence of such pinholes is determined by using a pinhole inspection apparatus in an inspection process of can bodies.

The pinhole inspection apparatus shown in Patent Document 1 is configured, as shown in FIG. 10, with an inspection turret that holds can bodies to be inspected on the right side, and an optical apparatus for inspecting the interior of can bodies on the left side. A piston-like sealing part is provided with a sealing ring plate fixedly attached thereto for sealing a sliding contact surface with a sliding ring plate by making sliding contact therewith. The piston-like sealing member is mounted on a distal end face of a first frame on the side facing the sliding ring plate for making the sliding contact. During pinhole inspection, the piston-like sealing part is pressed against the sliding ring plate rotating at high speed with air pressure, to enhance the sealing effect at the sliding contact surface, and to prevent ambient light, which consists of outside light and light from a light source, from reaching a photodetector side through the sliding contact surface.

Since the sealing ring plate is kept in pressure contact with the rapidly rotating sliding ring plate during pinhole inspection as noted above, ambient light normally does not reach the photodetector through the sliding contact surface between the sealing ring plate and the sliding ring plate. However, there was a possibility that ambient light may reach the photodetector through a gap that may be created instantaneously between the sealing ring plate and the sliding ring plate due to various factors such as some form of external force applied thereto, or the surface conditions of these plates, and good products may be erroneously determined as defective.

Patent Document 2 describes how to reduce stray light entering into an opening in a base member through a gap between a moving member and the base member by forming a V groove with inclined surfaces of different angles in a surface of one of a fixed disc and a rotating disc spaced apart from each other.

Patent Document 3 describes a light shield part made up of an annular, circumferentially oriented groove in a surface of a rotating disc opposite a movable plate, with a distal end portion of a fixed disc being located inside this circumferential groove. The light shield part allegedly prevents entrance of light emitted from a light source into a light guide path through between the fixed disc and the rotating disc.

In Patent Document 2, although a cover-like member is attached to peripheral and inner edge parts of the moving member, the fixed disc and the rotating disc are spaced apart from each other as a precondition. It is therefore assumed that, if a high lumen light source is employed for increasing pinhole inspection sensitivity, a significant amount of stray light would reach inside the opening where a photodetector is located due to diffused reflection on inner surfaces of the fixed disc and rotating disc.

The light shield part described in Patent Document 3 employs a complex structure wherein the fixed disc fits into the opposing circumferential groove, which makes position adjustment difficult. While the document discloses provision of a trap on the surface of the fixed disc to return the light to where it comes from, it does not fully explain the advantageous effects thereof and therefore fails to offer a complete solution to the problems mentioned above.

The diameter of pinholes to be inspected by a conventional pinhole inspection apparatus for can bodies is about 20 µm, which is determined by the performance of the photodetector. Pinholes with an even smaller diameter may not pass an enough amount of light into the can body to be detectable. A possible approach would be to secure a sufficient amount of light for enabling detection by the photodetector by using a light source with higher brightness than conventional light sources. However, the conventional apparatus configuration does not have sufficient countermeasures against ambient light, and the increase in the light amount could lead to an increased erroneous detection rate.

PRIOR ART LITERATURE

Patent Documents

Patent Document 1: Japanese Patent No. 4715988
Patent Document 2: Japanese Patent Application Laid-open No. 2002-365230
Patent Document 3: Japanese Patent No. 4230269

DISCLOSURE OF THE INVENTION

Problems to be Solved by the Invention

Based on the problems described above, a first object of the present invention is to provide a pinhole inspection apparatus for can bodies capable of effectively preventing ambient light from reaching a photodetector side through a gap between a rotary plate and a movable plate that may be formed due to external force or a surface condition or the like of a sealing ring plate and a sliding ring plate. A second object is to provide a pinhole inspection apparatus for can bodies with improved inspection precision, which is capable of detecting even smaller pinholes owning to the use of a light source with higher brightness that is enabled by achieving the first object.

Means for Solving the Problem

The present invention provides a pinhole inspection apparatus for can bodies including a rotary plate having a penetrating through hole, a movable plate provided on a stationary frame opposite the rotary plate, a can body holding member that holds a can body, a photodetector that detects light leaking inside the can body, and a light source that irradiates an outer circumferential surface of the can body with light. The movable plate includes a ring plate attached to a front surface of a piston member, which has a penetrating hole in a central portion thereof, via a joint member. The ring plate is provided with a shield member formed by an annular member that is formed concentric to the penetrating hole. The shield member is brought into sliding contact with the rotary plate by a pressure application mechanism.

The pinhole inspection apparatus for can bodies of the present invention may adopt the following forms:

1. The shield member is formed in plurality, and the pressure application mechanism is located to apply pressure evenly on respective surfaces of the shield members when the shield members are brought into sliding contact with the rotary plate.
2. A sliding member is fixed on surfaces of the ring plate and the shield member, and an annular groove concentric to the penetrating hole is formed in a surface of the sliding member.
3. A white LED light is used as the light source.
4. The can body holding member is secured to a support shaft of a chuck that holds the can body, via a rod such as to be movable with the chuck.
5. A detour path formed by a pair of shield parts spaced apart a predetermined distance and opposite from each other is provided as a shield mechanism in an entire outer peripheral region of the rotary plate.
6. The pair of shield parts is made up of a first shield part and a second shield part, the first shield part being fixedly attached to the rotating rotary plate, and the second shield part being fixedly attached to a position substantially opposite a side face part of the rotary plate.
7. The pair of shield parts include a first shield part and a second shield part, and shield elements provided to the respective shield parts protrude alternately toward tubular parts of the respective shield parts opposite each other.
8. The shield elements are shield plates protruding orthogonally to the tubular parts of respective shield parts opposite each other.

Effects of the Invention

With the pinhole inspection apparatus for can bodies of the present invention, the shield member formed by an annular member is brought into sliding contact with the rotary plate by the pressure application mechanism during pinhole inspection, so that ambient light penetrating through a gap between the rotary plate rotating at high speed and the movable plate can be shielded, and can be effectively prevented from reaching the photodetector side.

With the shield member being formed in plurality, the ambient light shield effect is improved or enhanced. Moreover, since the pressure application mechanism is located to apply pressure evenly on respective surfaces of the shield members when the shield members are brought into sliding contact with the rotary plate, frictional force generated by sliding of respective shield members is made uniform, so that mechanical fatigue of the rotary plate and shield members can be reduced.

With a sliding member fixed on surfaces of the ring plate and the shield member, and with an annular groove concentric to the penetrating hole being formed in a surface of the sliding member fixed on the shield member, sliding with the rotary plate is made smoothly. Moreover, light is attenuated or absorbed every time the light reaches the space in the annular groove, so that the amount of light that reaches the penetrating hole formed in the movable plate can be effectively reduced, and the ambient light is effectively prevented from reaching the photodetector side.

Since the pinhole inspection apparatus for can bodies of the present invention can employ a high lumen light source, it can use a white LED light instead of the conventional fluorescent light as the light source for irradiating an outer circumferential surface of the can body with light, so that the apparatus can detect pinholes with an even smaller diameter (of about several μm), while effectively preventing ambient light from reaching the photodetector side.

With the use of a can body holding member fixed to a support shaft of a chuck that holds the can body, via a rod such as to be movable with the chuck, a holder turret is made unnecessary, so that the degree of freedom for installing the light source (in particular, lower light source) for irradiating the can body with light is increased, and therefore it is possible to provide more light sources to increase the light amount. Also, defects such as scars or dents in the body part of the can body, which may result from sliding with an end face of a pocket of the holder turret as the can body moves axially relative to the rotary plate, can be prevented.

The pinhole inspection apparatus for can bodies of the present invention additionally includes a complex structured detour path provided as a shield mechanism, so that it is possible to attenuate or shield ambient light as the light propagates through the detour path, and to effectively prevent entrance of ambient light to the photodetector side through a gap between the movable plate and the rotary plate.

The pair of shield parts include a first shield part and a second shield part, the first shield part being fixedly attached to the rotating rotary plate, and the second shield part being fixedly attached to an end of a case that covers a stationary frame, whereby the pair of shield parts can have a stable predetermined distance, which enables stable attenuation or shielding of ambient light as the light propagates through the detour path, and effectively prevents contact between the shield parts.

As the shield elements provided to the first shield part and second shield part protrude alternately toward tubular parts of respective shield parts opposite each other, the propagation path of ambient light is made long, so that ambient light can be effectively attenuated or shielded.

Since the shield elements are formed as shield plates that protrude orthogonally toward the tubular parts of the respective shield parts opposite each other, the pair of shield parts that are arranged opposite each other can be readily attached, and also, contact between the shield parts can be prevented. With the shield elements formed as thin shield plates, the number of shield elements formable on the respective shield parts can be increased, to make the detour path even more complex within a limited range, whereby the effect of attenuating or shielding ambient light can be increased even more.

EXPLANATION OF REFERENCE NUMERALS

Figure 1:
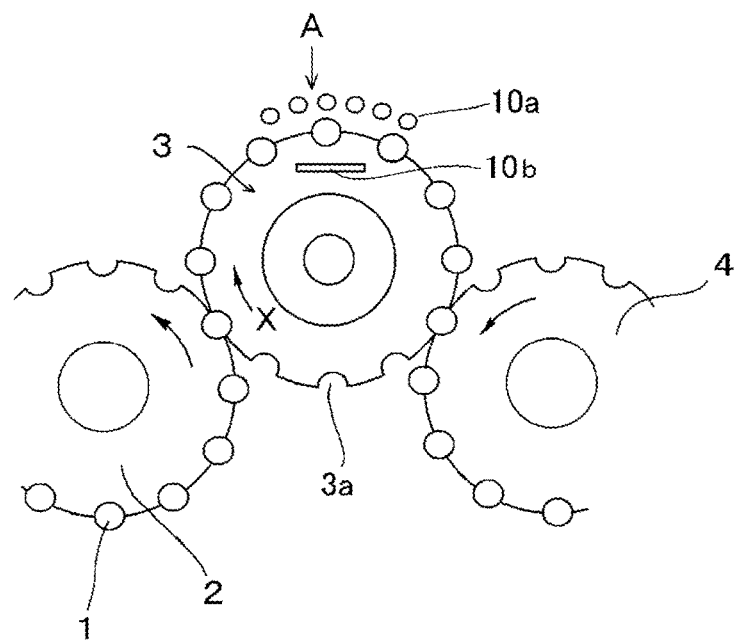
FIG. 1 is a schematic diagram for explaining one form of inspecting can bodies with a pinhole inspection apparatus for can bodies of the present invention.

1: Can body
2: Feed-in turret
3: Holder turret
3a: Pocket
3h: Can body holding member
3r: Rod
4: Feed-out turret
5: Rotary plate
6: Chuck
7: Open end receiving part
7a: Attachment ring
9: Support shaft
10: Light source
10a, 10b: Upper and lower light sources
11: Stationary frame
12: Casing
13: Photodetector (photomultiplier tube)
20: Movable plate
22: Piston member
25: Ring plate
26a, 26b: Sliding member
27: Joint member
28: Screw hole
30: Shield mechanism
31: Shield member
32: Pressure application mechanism
33: Piston rod
34: Fitting groove
35: Annular flow passage
36: Supply hole
37: Slide hole
38: Communication hole
39: Annular groove
40: Rotating shield part
41: Tubular part
42a, 42b: Shield element
50: Fixed shield part
51: Tubular part
52a, 52b: Shield element

MODES FOR CARRYING OUT THE INVENTION

One embodiment of a pinhole inspection apparatus for can bodies of the present invention will be described.

As shown in FIG. 1, in the pinhole inspection apparatus for can bodies of the present invention, a can body 1 is supplied by a feed-in turret 2 to a pocket 3a of a holder turret 3 that rotates continuously in direction X, and transferred to an inspection station A where an upper light source 10a and a lower light source 10b (hereinafter also referred to as light source 10) to be described later are located to be checked if it is good, after which the can body is conveyed further to a next process by a feed-out turret 4.

Figure 2:
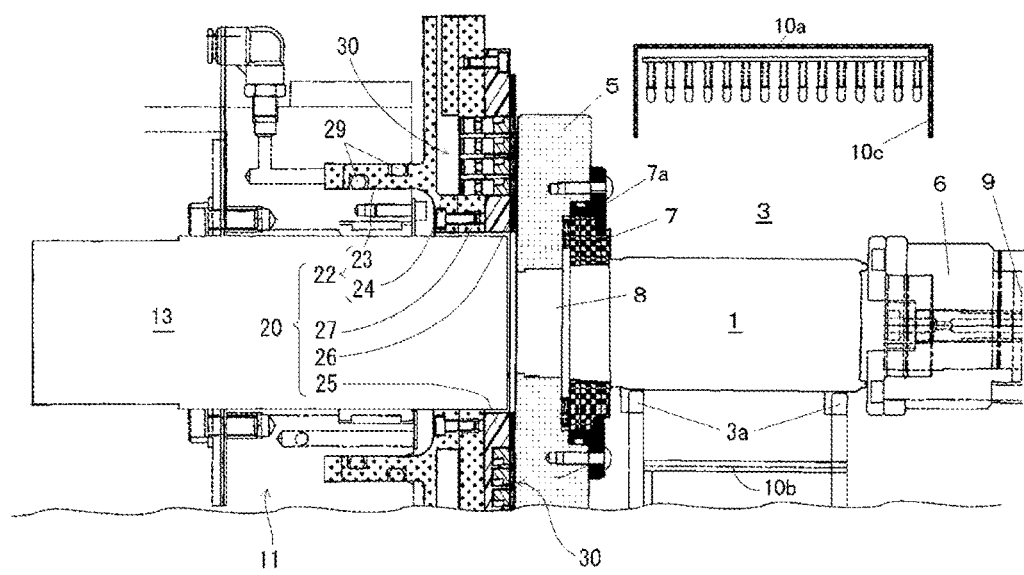
FIG. 2 is a diagram illustrating an inspection region of the pinhole inspection apparatus for can bodies of the present invention.

As shown in FIG. 2, the pinhole inspection apparatus for can bodies of the present invention includes the holder turret 3, a rotary plate 5, a chuck 6, and the upper and lower light sources 10a and 10b. The holder turret 3 and the rotary plate 5 constitute an inspection turret. The holder turret 3 is a can body holding member that places a can body 1 coaxially with a hole 8 in the rotary plate 5 to be described later, as the can body moves past the inspection station A, and formed with a plurality of pockets 3a, or recesses where the body part of the can body 1 is placed, along the outer peripheral edge thereof.

The rotary plate 5 has a plurality of holes 8 extending through both sides thereof. An open end receiving part 7 of a sponge material, to which the open end of an open-ended can body 1 is pressed, is attached to one peripheral edge of the hole 8 via an attachment ring 7a.

The chuck 6 is a member that holds the bottom of the can body 1 by vacuum suction, and fixedly attached on a support shaft 9 and arranged opposite the rotary plate 5. The chuck 6 and the support shaft 9 are axially movable relative to the rotary plate 5 to bring the open end of the can body 1 into tight contact with the open end receiving part 7 integral with the rotary plate 5 by means of a cam and a cam follower (not shown). The can body 1 is moved axially such as to slide on the pocket 3a. The support shaft 9 is attached to a component fixed on the rotating shaft of the rotary plate 5 via a slide mechanism or the like (not shown) and located substantially opposite the hole 8 in the rotary plate 5.

Inside a stationary frame 11 is provided a highly sensitive photodetector 13 (such as a photomultiplier tube) opposite the rotary plate 5 and coaxially with the hole 8 and a penetrating hole 21 of a movable plate 20 to be described later to detect light leaking inside the can body 1.

In this configuration, as the light source 10, the upper light source 10a and lower light source 10b are arranged for illuminating a body part of the can body 1 from above and below when the can body 1 that is held and supported by the pocket 3a of the holder turret 3 and the chuck 6 has moved to a position opposite the photodetector 13 set in the stationary frame 11 (inspection station A). A cover 10c is attached to the light source 10a for preventing light from the light source from leaking to the outside of the apparatus.

The light source for this type of pinhole inspection should preferably emit white light including the whole range of wavelengths from ultraviolet light to infrared light. This embodiment employs a plurality of arrayed white LED lights as a high lumen light source. This allows for detection of pinholes of even smaller diameter with improved inspection precision, while access of ambient light to the photodetector 13 side is effectively prevented by the shield mechanism to be described later.

During inspection of can bodies 1 successively conveyed by continuous rotation, the can body 1 held in the pocket 3a of the holder turret 3 is rotatably supported by the chuck 6, with its open end being in tight contact with the open end receiving part 7 of the rotary plate 5. The can body 1 is then illuminated by the light sources 10a and 10b in the inspection station A, and when the hole 8 of the rotary plate 5 comes to be coaxial with the penetrating hole 21 of the movable plate 20 (sensing position), light leaking into the can body 1 is received by the photodetector 13, and presence or absence of a pinhole is determined based on the amount of light.

Figure 3:
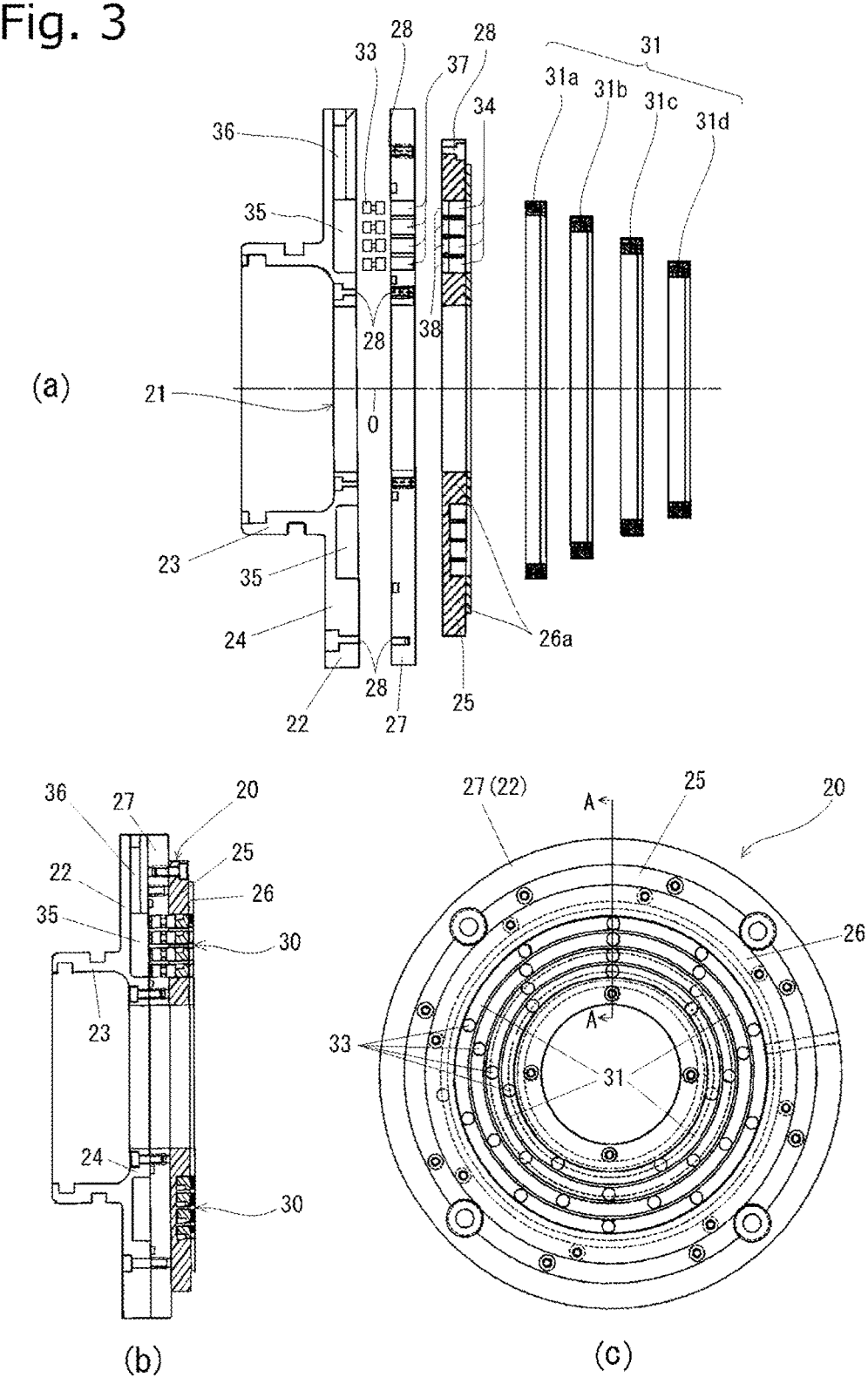
FIG. 3A is an exploded cross-sectional view.
FIG. 3B is a cross-sectional view.
FIG. 3C is a plan view of various components of major part including a shield mechanism of the present invention.

The movable plate 20 is a circular component arranged opposite the rotary plate 5 and fixed at a suitable position by means of fixing screw holes 28 and bolts, and includes a ring plate 25 attached on the front surface of a piston member 22 that has the penetrating hole 21 in the center via a joint member 27. The movable plate is described in more detail below with reference to FIG. 2 and FIG. 3.

The piston member 22 is made up of a tubular leg 23 and a top plate 24 as shown in FIG. 2. The leg 23 is fitted in a fitting guide groove formed in the stationary frame 11 so that it can reciprocate to and from the rotary plate 5 by pneumatic piston action. With such a configuration, the movable plate 20 is pressed to make sliding contact with the rotary plate 5 to seal the sliding contact surface, so that ambient light is prevented from reaching the photodetector 13 side from the sliding surface. As shown in FIG. 3A, an annular flow passage 35 coaxial with the penetrating hole 21 and having a recessed cross section is formed on one side of the piston member 22 that faces the joint member 27 to be described later, and a supply hole 36 that communicates with this annular flow passage 35 and extends from an inner side of the piston member 22 to the outer circumferential surface is connected to an air supply device (not shown).

As shown in FIG. 3A, a plurality of slide holes 37 are formed in the joint member 27 at suitable positions corresponding to the annular flow passage 35 in the piston member 22 when the joint member 27 is assembled to the front surface of the piston member 22 for piston rods 33 to freely slide therein. The slide holes 37 are spaced a certain distance apart along a plurality of (four in this embodiment) imaginary circles concentric to the center O of the penetrating hole 21 in the piston member 22 with different radii.

On the other hand, the ring plate 25 has fitting grooves 34 with a recessed cross section that are concentric to the penetrating hole 21 in the piston member 22 and extend in register with the plurality of imaginary circles. Communication holes 38 having the same diameter as that of the slide holes 37 of the joint member 27 are formed at positions corresponding to the slide holes 37.

The movable plate 20 is an assembly of these piston member 22, joint member 27, and ring plate 25, wherein the annular flow passage 35 in the piston member 22, the slide holes 37 in the joint member 27, and the communication holes 38 in the fitting grooves 34 of the ring plate 25 are in fluid communication with each other. Shield members 31 that form the shield mechanism 30 to be described later are configured to be pressed by the piston rods 33 that slide inside the slide holes 37 of the joint member 27. A sliding member 26a made of a black, non-gloss, and relatively soft plastic with a low friction coefficient, such as a fluorine resin soft plastic, is securely bonded to the ring plate 25 on the side that faces the rotary plate 5 with non-transparent adhesive to ensure smooth sliding with the rotary plate 5.

The shield mechanism 30 in the pinhole inspection apparatus for can bodies of the present invention is made up of the shield members 31 and a pressure application mechanism 32.

The shield members 31 of the shield mechanism 30 are an annular component concentric to the penetrating hole 21 in the movable plate 20 and having a rectangular cross section as shown in FIG. 3A to FIG. 3C and FIG. 4, which are fitted in the fitting grooves 34 in the ring plate 25. The plurality of piston rods 33 that slide inside the slide holes 37 of the joint member 27 are positioned on the back side of the shield members 31. Similarly to the rotary plate 5 side of the ring plate 25, a sliding member 26b made of a black, non-gloss, and relatively soft plastic with a low friction coefficient, such as a fluorine resin soft plastic, is secured to one side of the shield members 31 that faces the rotary plate 5 with non-transparent adhesive to ensure smooth sliding with the rotary plate 5.

Figure 4:
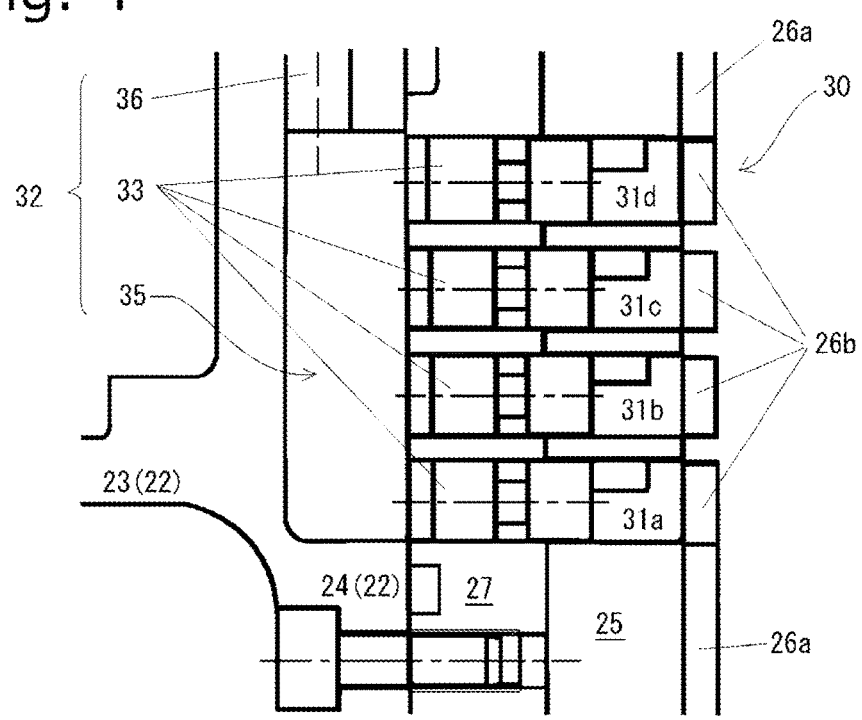
FIG. 4 is an enlarged view of major part of the shield mechanism of the present invention.

The pressure application mechanism 32 is made up of the piston rods 33, annular flow passage 35, supply hole 36, and an air supply device (not shown), as shown in FIG. 3B and FIG. 4, to allow the piston rods 33 to move back and forth pneumatically, so that the shield members 31 described above are pressed against and slides on the rotary plate 5.

With this configuration, the shield members 31 are pressed against the rotary plate 5 to make sliding contact therewith during inspection of can bodies for pin holes, to shield ambient light penetrating through a gap between the rotary plate 5 and the movable plate 20.

In this embodiment, four shield members 31 (31a, 31b, 31c, and 31d) are concentrically arranged. As shown in FIG. 3C, the shield member 31a has seven piston rods 33, the shield member 31b has eight piston rods 33, the shield member 31c has nine piston rods 33, and the shield member 31d has ten piston rods 33, all circumferentially equally spaced from each other.

This improves or enhances the ambient light shield effect described above, makes the surface pressure between the rotary plate 5 and respective shield members 31a to 31d in sliding contact therewith even, and also makes the friction resulting from the sliding contact of the shield members 31a to 31d even, so that mechanical fatigue of the rotary plate 5 and the shield members 31 can be reduced.

Figure 5:
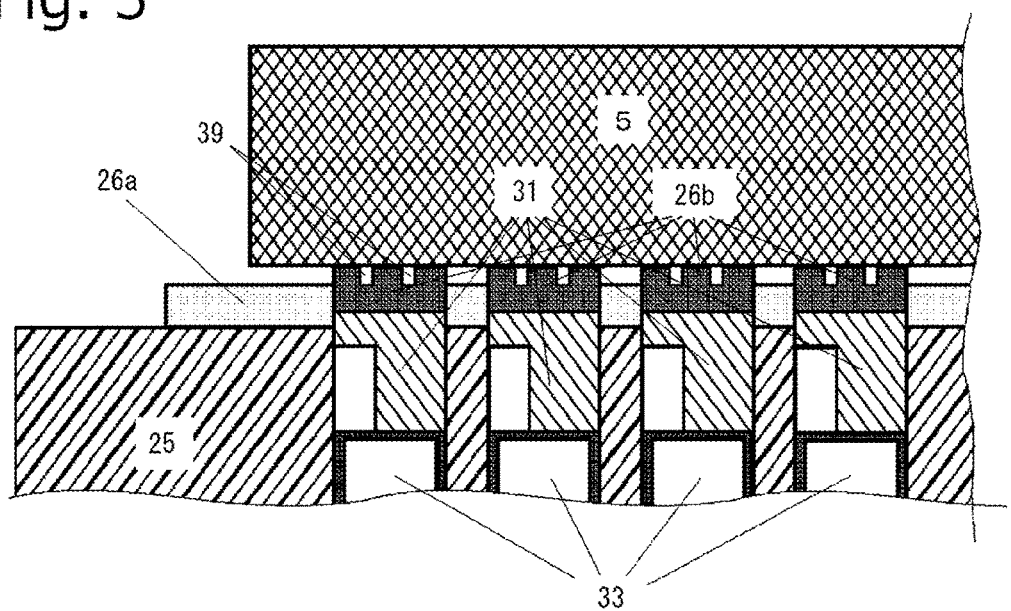
FIG. 5 is a partial enlarged view of a cross section A-A of FIG. 3C of the shield mechanism of the present invention.

FIG. 5 is an enlarged partial cross-sectional view of the shield members 31 and the rotary plate 5 taken along A-A of FIG. 3C, which shows that the movable plate 20 is disposed with a small gap between the sliding member 26a on the ring plate 25 and the rotary plate 5, and that the four shield members 31a to 31d pressed by the pressure application mechanism 32 are in sliding contact with the rotary plate 5. The shield members only may make sliding contact with the rotary plate 5 in this way, instead of the entire surface of the movable plate making sliding contact with the rotary plate 5, in which case, not only the mechanical fatigue resulting from the sliding contact can be alleviated, but also an erroneous operation of the photodetector that may be caused by vibration due to friction on sliding surfaces, or friction heat, can be effectively prevented.

Alternatively, the movable plate 20 may be pressed against the rotary plate 5 to bring the entire surface of the movable plate 20 into sliding contact therewith, while the shield members 31 are pressed by the pressure application mechanism 32, to make even tighter sliding contact, and to shield ambient light penetrating through between the movable plate 20 and the rotary plate 5.

As shown in FIG. 5, a plurality of annular grooves 39 concentric to the penetrating hole 21 of the movable plate 20 and having a rectangular cross section may be formed in the sliding member 26b fixed on the surface of each shield member 31. Light is attenuated or absorbed every time it reaches the space inside the annular grooves 39 having a rectangular cross section formed in the sliding member 26b, so that the amount of light that reaches the penetrating hole 21 formed in the movable plate 20 is effectively reduced, and thus ambient light is effectively prevented from reaching the photodetector 13 side. The annular grooves 39 may be formed in the sliding member 26a, or, alternatively, the sliding member 26a between the sliding members 26b may be left unbonded so that there are formed gaps between the rotary plate 5 side of the ring plate 25 and the sliding members 26b to function as annular grooves 39.

Figure 6:
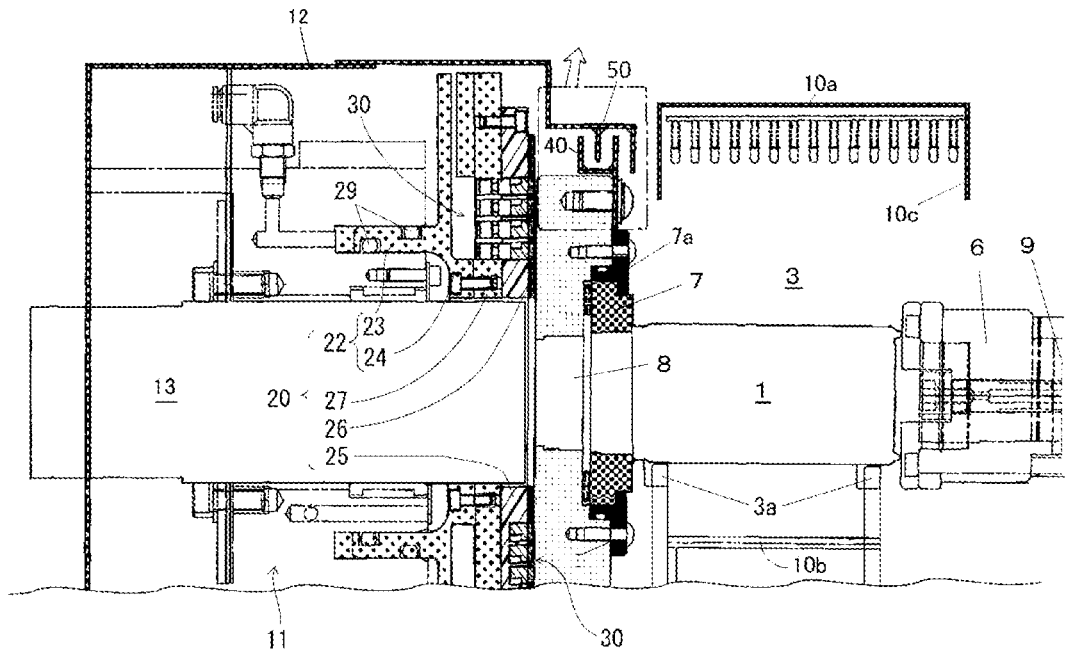
FIG. 6 is a diagram illustrating one form in which a second shield mechanism formed by a pair of shield parts spaced apart a predetermined distance and opposite from each other is provided in an entire outer peripheral region of a rotary plate.

FIG. 6 is a diagram showing a pinhole inspection apparatus for can bodies of the present invention additionally having a second shield mechanism, which has a detour path formed by a pair of shield parts spaced apart a predetermined distance and opposite from each other, and which is provided in an entire outer peripheral region of the rotary plate as a shield mechanism. In this embodiment, a detour path formed by a pair of shield parts spaced apart a predetermined distance and opposite from each other is provided as a shield mechanism in an entire outer peripheral region of the rotary plate. That is, with a complex structured detour path provided as the shield mechanism, it is possible to attenuate or shield ambient light as the light propagates through the detour path, whereby entrance of ambient light to the photodetector side from between the movable plate 20 and the rotary plate 5 is effectively prevented.

As shown in FIG. 6, the pair of shield parts are made up of a rotating shield part 40 attached to the rotary plate 5 by bolts or the like, and a fixed shield part 50 fixedly attached to a position substantially opposite a side face part of the rotary plate 5, which is, in this embodiment, a distal end of the casing 12 that covers the stationary frame 11. This way, the pair of shield parts can have a stable predetermined distance, which enables stable attenuation or shielding of ambient light as the light propagates through the detour path, and effectively prevents contact between the shield parts.

More specifically, the rotating shield part 40 includes a tubular part 41 that surrounds an entire outer peripheral region of the rotary plate 5 and extends a predetermined length along a thickness direction of the rotary plate 5, and a plurality of shield elements 42a and 42b attached to protrude from the surface of the tubular part 41 toward the fixed shield part 50. The fixed shield part 50 includes a tubular part 51 that surrounds an outer peripheral region of the side face part of the rotary plate 5 and extends a predetermined length along the thickness direction of the rotary plate 5, and a plurality of shield elements 52a and 52b attached to protrude from the surface of this tubular part 51 toward the rotating shield part 40.

The rotating shield part 40 and fixed shield part 50, i.e., the tubular parts 41 and 51, and respective shield elements 42a and 42b, and 52a and 52b (hereinafter referred to as shield elements 42 and 52), are spaced a predetermined distance apart so as not to contact each other while facing each other, so that they do not interfere with rotation of the rotary plate 5. This shield mechanism is made of a metal material such as iron plate or the like, with a non-gloss, black surface treatment to absorb, and reduce reflectivity of, ambient light.

Figure 7:
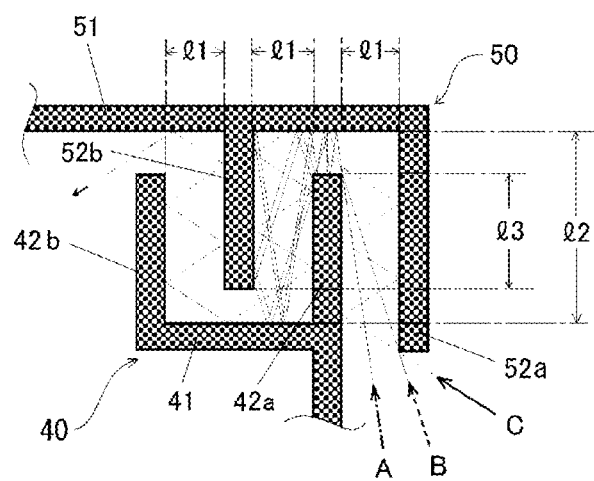
FIG. 7 is a diagram for explaining the shielding function of the second shield mechanism of the present invention.

The effect of the shield mechanism formed by the rotating shield part and fixed shield part of the present invention will be discussed with reference to FIG. 7.

In this embodiment, shield elements 42 are attached to two locations (42a, 42b) of the rotating shield part 40, and shield elements 52 are attached to two locations (52a, 52b) of the fixed shield part 50 such as to alternately protrude to the respective tubular parts of the opposite shield parts, with a distance 11 between one shield element and another shield element opposite thereto. With such a configuration, the propagation path of ambient light can be formed long, so that ambient light can be effectively attenuated or shielded.

Since the shield elements 42 and 52 are formed as shield plates that protrude orthogonally toward the respective tubular parts 41 and 51 of the opposite shield parts 40 and 50, the pair of shield parts 40 and 50 that are arranged opposite each other can be readily attached, and also, contact between the shield parts 40 and 50 can be prevented. With the shield elements 42 and 52 formed as thin shield plates, the number of shield elements 42 and 52 formable on the respective shield parts 40 and 50 can be increased, to make the detour path even more complex within a limited range, whereby the effect of attenuating or shielding ambient light can be increased even more.

The shorter the distance 11 is, the higher the light shielding effect, and the more the shield elements 42 and 52 are provided, the higher the light shielding effect. The shield elements 42 and 52 have a length of ½ or more of a distance 12 between the tubular parts 41 and 51, so that shield elements 42a and 42b overlap the opposing shield elements 52a and 52b. The longer the overlapping length 13 is, the higher the light shielding effect.

In this embodiment, with the distance 11 being 5 mm or less, and with the overlapping length 13 being 9 mm or more when the distance 11 is 5 mm, the propagation path in the detour path can be made narrow, while contact between the rotating shield part 40 and fixed shield part 50 that may occur due to rotation of the rotary plate 5 is prevented, so that ambient light can be effectively attenuated or shielded. With the distance 11 being more than 5 mm, the propagation path in the detour path will be wide, and if the overlapping length 13 is less than 9 mm, the propagation path in the detour path will be short, and in both cases it may be difficult to effectively attenuate or shield ambient light.

The shield elements 42 and 52 may have a length, distance, and angle suitably set within such a range that they will not inhibit rotation of the rotary plate 5.

Ambient light to be shielded is the direct light projected from the upper light source 10a and lower light source 10b, and reflected light from the can body 1 or various parts of the pinhole inspection apparatus, and ambient light entering into the shield mechanism formed by the rotating shield part 40 and the fixed shield part 50 is illustrated as light beams A, B, and C from below in FIG. 7. Using these light beams from three directions as samples, how a light beam in a specular direction propagates, which is reflected most strongly according to the Gaussian distribution, will be discussed. In FIG. 6, from the light sources 10a and 10b side, the region between the shield element 52a and the shield element 42a will be referred to as first region, the region between the shield element 42a and the shield element 52b will be referred to as second region, the region between the shield element 52b and the shield element 42b will be referred to as third region, and the region from the shield element 42b further on will be referred to as fourth region.

Light beam A is incident at a small angle to the surface of the shield element 42a, reflected several times between an inner surface of the tubular part 51 of the fixed shield part 50 and the distal end face of the shield element 42a, after which it is reflected several times inside the second region. Namely, light beam A cannot go beyond the second region. Provided that the reflectivity is 1/n, the light amount after it is reflected ten times, for example, is $(1/n)^{10}$ of the incident light amount, which is sufficiently low.

Light beam B is incident at a slightly larger angle to the surface of the shield element 42a, and similarly reflected several times between the inner surface of the tubular part 51 of the fixed shield part 50 and the distal end face of the shield element 42a, after which it is reflected several times inside the second region, bouncing off the shield element 52b. Namely, light beam B cannot go beyond the second region, either, and the light amount after it is reflected ten times, for example, is $(1/n)^1$ of the incident light amount, which is sufficiently low.

Light beam C is incident at a large angle to the surface of the shield element 42a, reflected several times inside the first region, after which it enters the second region via the inner surface of the tubular part 51 and is reflected several times inside the second region. It then enters the third region via an outer surface of the tubular part 41 and is reflected several times inside the third region, and reaches the fourth region, again via the inner surface of the tubular part 51. Namely, light beam C reaches the fourth region, which should actually be prevented, but since it is reflected many times inside the shield mechanism (fifteen times in this embodiment), the light amount is $(1/n)^{15}$ of the incident light amount, which is even lower than that of light beams A and B, whose light amount is sufficiently low. Therefore, even if there is created a gap instantaneously between the movable plate 20 and the rotary plate 5, an erroneous operation of the photodetector 13 by light beam C (ambient light) can be effectively prevented, as compared to the conventional configuration.

With the shield mechanism of the present invention, as can be seen from the analysis of the reflection behaviors of the three sample light beams, ambient light that has entered the first region cannot easily reach the fourth region because of the reflection phenomenon. Also, as mentioned above, at least the surfaces of the rotating shield part 40 and fixed shield part 50 (surfaces forming the detour path) have a black, non-gloss surface treatment, it is reasonable to understand that the reflected light is scattered, i.e., the reflected light is actually scattered in all directions on the surfaces of the rotating shield part 40 and fixed shield part 50 and this scattering is repeated. Therefore, the amount of propagated light will be reduced successively from the first region to the second region, and from the second region onwards.

The shield mechanism of the present invention may be changed variously.

Figure 8:
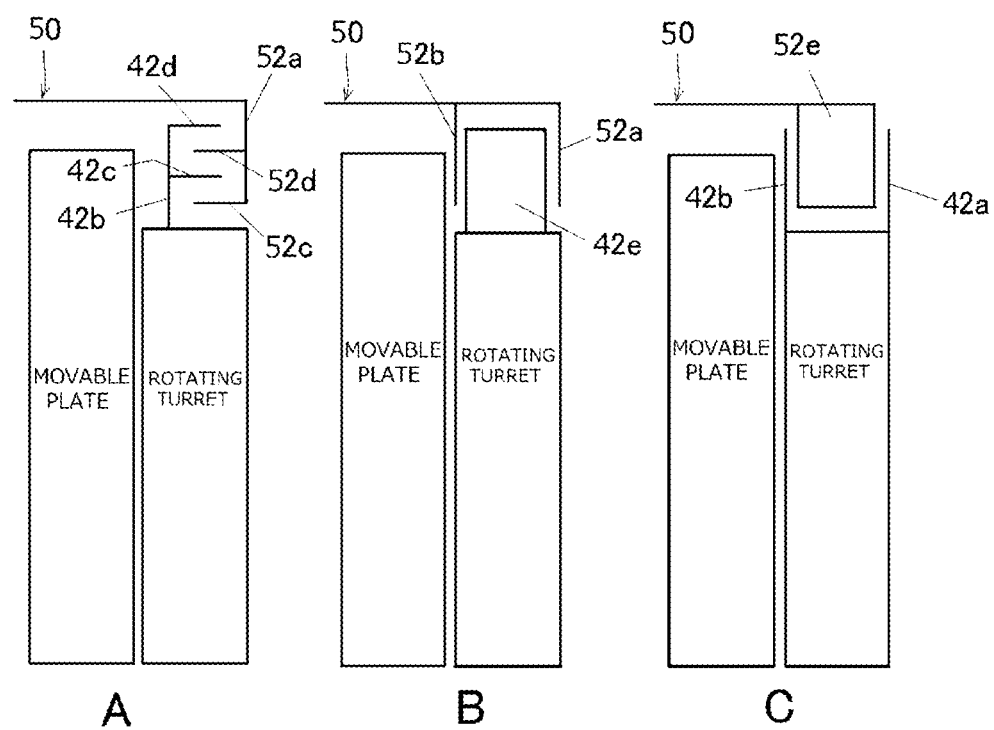
FIG. 8A to FIG. 8C are diagrams illustrating variation examples of the second shield mechanism of the present invention.

For example, as shown in FIG. 8A to FIG. 8C, the length of the shield element 42a may be extended to near the bolt for attaching the rotating shield part 40, to make the propagation path of ambient light longer, so that ambient light can be effectively attenuated or shielded.

As shown in FIG. 8A, additional shield elements 52c and 52d, and shield elements 42c and 42d, which protrude upright to each other, may be formed between the shield element 52a and shield element 42a (in the first region), with the distance 11 therefrom.

As shown in FIG. 8B, the respective tubular parts and shield elements of the rotating shield part 40 and fixed shield part 50 can be formed by components with a suitable thickness within a certain range as long as they do not inhibit rotation of the rotary plate 5. For example, the rotating shield part 40 may be an annular block 42e, and arranged between the shield elements 52a and 52b of the fixed shield part 50 with the distance 11 therefrom. Conversely, as shown in FIG. 8C, the fixed shield part 50 may be configured as an annular block 52e.

Further, the respective tubular parts and shield elements of the rotating shield part 40 and fixed shield part 50 may have irregularities on their surfaces (such as recessed grooves), whereby ambient light that has entered the shield mechanism can be scattered even more, and an even higher light shielding effect can be achieved.

As described above, the shield mechanism of the present invention can employ a variety of forms with a high light shielding effect in accordance with the apparatus configuration and desired light shielding effect.

Thereby, defects resulting from sliding movement, such as scars or dents on the can body 1, for example, can be prevented.

Next, test data that shows the light reducing effect of the second shield mechanism of the present invention will be shown.

Various constituent elements of the shield mechanism are made from a 2 mm thick iron plate with a black, non-gloss surface treatment, with dimensions set as follows:
<Rotating Shield Part 40>
Length of tubular part 41=15 mm
Length of shield elements 42a and 42b=12 mm
<Fixed Shield Part 50>
Length of tubular part 51=30 mm
Length of shield element 52a=17 mm
Length of shield element 52b=12 mm
<Others>
Distance 11: 5 mm
Distance 12: 15 mm
Overlapping length 13: 9 mm A can body 1 was held in one given pocket 3a of the holder turret 3 in the pinhole inspection apparatus for can bodies of the present invention, and the open end of the can body 1 was brought into contact with the open end receiving part 7. The rotary plate 5 is rotated gradually and positioned such that the hole 8 in the rotary plate 5 is coaxial with the penetrating hole 21 in the movable plate 20, whereupon the rotary plate 5 is stopped to perform the test for ascertaining the light reducing effect. To confirm the light shielding effect of the shield mechanism of the present invention, the air cylinder for pressing the movable plate 20 was not operated on purpose so that there was a gap of 0.08 mm between the movable plate 20 and the rotary plate 5. Measurement was made using a photodetector 13 in embodiments of the present invention with the shield mechanism, and conventional counterparts without the shield mechanism as comparative examples.

The average value of light detection measurements was 125 mV in the embodiments of the present invention, with a maximum instantaneous value being 220 mV, while it was 4900 mV or more (which was the upper measurement limit of the photodetector) in the comparative examples.

The gap between the movable plate 20 and the rotary plate 5 was set to 0.08 mm so that the light reducing effect would be more evidently perceived. The light reducing effect will be even higher if the gap is made even smaller.

According to the embodiment, as described above, entrance of ambient light to a photodetector side through a gap between a movable plate and a rotary plate that may be formed due to a surface condition or the like can be effectively prevented.

The increased light shielding effect of the present invention enables use of a light source having even higher brightness and detection of pinholes with an even smaller diameter (of about several μm), and thus a pinhole inspection apparatus for can bodies with improved inspection precision can be provided.

Moreover, as long as a desired degree of light reducing effect is achieved, the gap between the movable plate and rotary plate may be set such that they do not contact each other during detection operation, which not only prevents apparatus fatigue caused by sliding between the movable plate and rotary plate, but also resolves the conventional problem of erroneous operation of the photodetector resulting from vibration and heat generated by friction on the sliding surfaces. This will in turn significantly increase the accuracy and efficiency of pinhole inspection operation.

Figure 9:
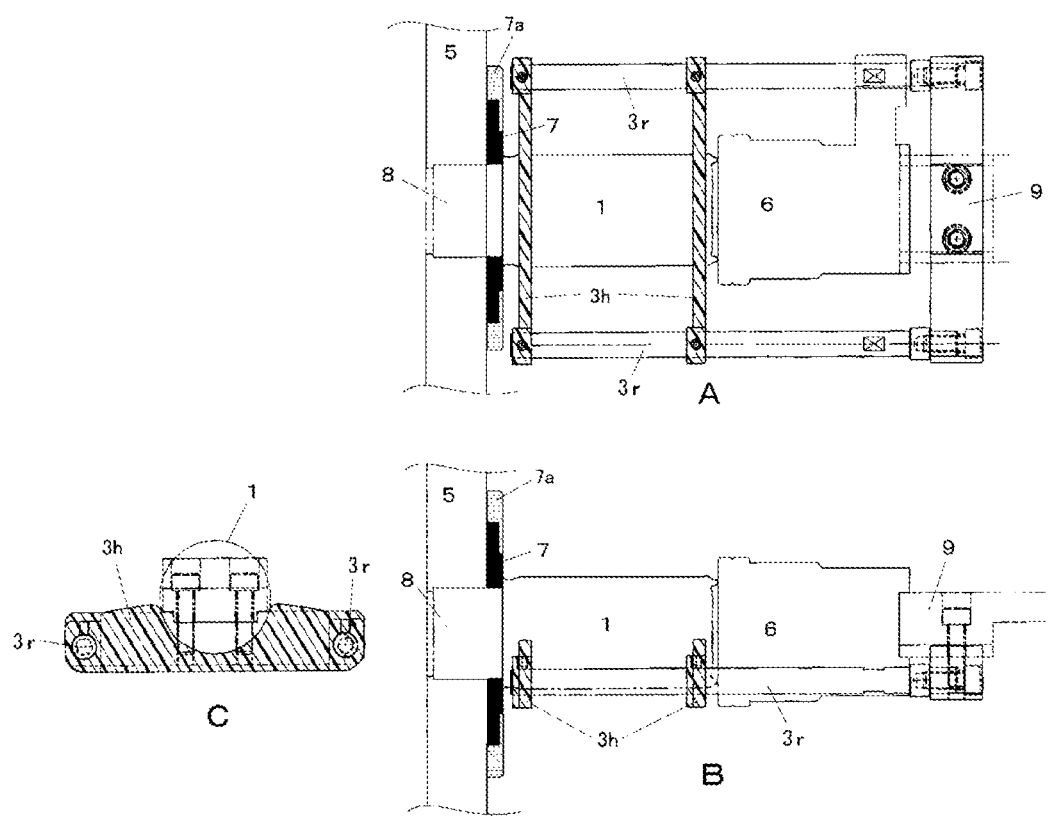
FIG. 9A to FIG. 9C are diagrams illustrating a mechanism for holding can bodies applicable to the present invention.
Figure 10:
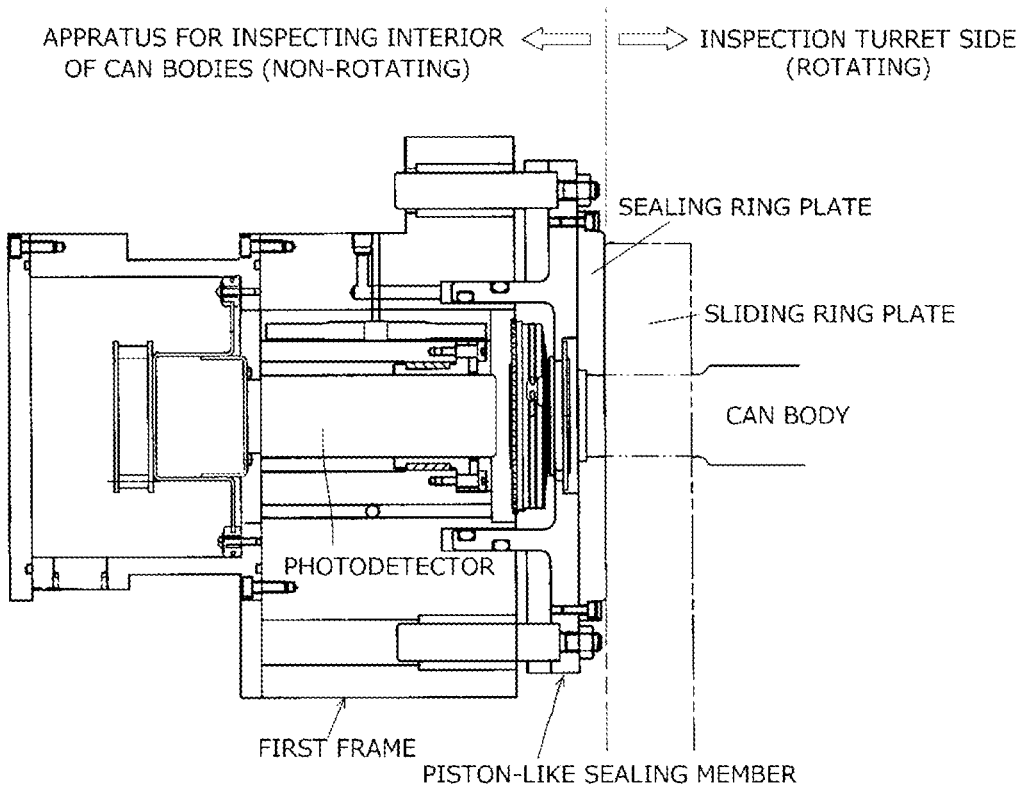
FIG. 10 is a diagram for explaining the configuration of a conventional pinhole inspection apparatus for can bodies.

FIG. 9A to FIG. 9C illustrate can body holding members 3h that may be used in place of the holder turret 3 of the previously described embodiment of the present invention. FIG. 9A is a bottom view, FIG. 9B is a front view, and FIG. 9C is a side view of can body holding members 3h holding a can body 1.

The can body holding members 3h are a plate-like component having a recess in an upper part in which the can body 1 can be placed. They are secured to a support shaft 9 of the chuck 6 via rods 3r that supports the can body 1. The can body holding members 3h are attached on a plurality of rods 3r with a predetermined distance therebetween so as to hold near upper end and lower end of the body part of the can body 1. The can body holding members 3h and the chuck 6 are movable along an axial direction relative to the rotary plate 5 as they hold the can body 1, to bring the open end of the can body 1 into tight contact with the open end receiving part 7 of the rotary plate 5 by means of a cam and a cam follower (not shown).

With the use of such can body holding members 3h, the holder turret 3 described in the foregoing is made unnecessary, so that the degree of freedom for installing the light source 10 (in particular, lower light source 10b) for irradiating the can body 1 with light is increased, and it is possible to provide more light sources to increase the light amount. Also, defects such as scars or dents in the body part of the can body 1, which may result from sliding with an end face of the pocket 3a of the holder turret 3 as the can body 1 moves axially relative to the rotary plate 5, can be prevented.

As described above, according to the present invention, ambient light can be effectively prevented from reaching a photodetector side through a gap between a movable plate and a rotary plate that may be formed due to external force, or a surface condition of a sealing ring plate and a sliding ring plate.

The increased light shielding effect enables use of a light source with higher brightness and detection of pinholes with an even smaller diameter (of about several μm), and thus a pinhole inspection apparatus for can bodies with improved inspection precision can be provided.

With the use of the form that includes the second shield mechanism, light that reaches between the rotary plate and movable plate can effectively be shielded in the first place, so that access of ambient light to the photodetector side can be prevented even more effectively.

Moreover, as long as a desired degree of light reducing effect is achieved, the gap between the movable plate and rotary plate may be set such that they do not contact each other during detection operation, which not only prevents mechanical fatigue caused by sliding between the movable plate and rotary plate, but also resolves the conventional problem of erroneous operation of the photodetector resulting from vibration and heat generated by friction on the sliding surfaces. This will in turn significantly increase the accuracy and efficiency of pinhole inspection operation.

The invention claimed is:

1. A pinhole inspection apparatus for can bodies comprising: a rotary plate having a penetrating through hole; a movable plate provided on a stationary frame opposite the rotary plate; a can body holding member that holds a can body; a photodetector that detects light leaking inside the can body; and a light source that irradiates an outer circumferential surface of the can body with light, wherein
the movable plate includes a ring plate attached to a front surface of a piston member via a joint member, the piston member having a penetrating hole in a central portion thereof,
the ring plate is provided with a shield member formed by an annular member that is formed concentric to the penetrating hole, and
the shield member is brought into sliding contact with the rotary plate by a pressure application mechanism.

2. The pinhole inspection apparatus for can bodies according to claim 1, wherein the shield member is formed in plurality, and the pressure application mechanism is located to apply pressure evenly on respective surfaces of the shield members when the shield members are brought into sliding contact with the rotary plate.

3. The pinhole inspection apparatus for can bodies according to claim 1, wherein a sliding member is fixed on surfaces of the ring plate and the shield member, and an annular groove concentric to the penetrating hole is formed in a surface of the sliding member fixed on the shield member.

4. The pinhole inspection apparatus for can bodies according to claim 1, wherein the light source is a white LED light source.

5. The pinhole inspection apparatus for can bodies according to claim 1, wherein the can body holding member is secured to a support shaft of a chuck that holds the can body, via a rod such as to be movable with the chuck.

6. The pinhole inspection apparatus for can bodies according to claim 1, wherein a detour path formed by a pair of shield parts spaced apart a predetermined distance and opposite from each other is provided as a shield mechanism in an entire outer peripheral region of the rotary plate.

7. The pinhole inspection apparatus for can bodies according to claim 6, wherein the pair of shield parts are made up of a rotating shield part and a fixed shield part, and shield elements provided to the respective shield parts protrude alternately toward tubular parts of the respective shield parts opposite each other.

* * * * *